US008279061B2

(12) United States Patent
Soliman

(10) Patent No.: US 8,279,061 B2
(45) Date of Patent: Oct. 2, 2012

(54) TELEMEDICINE APPLICATION FOR REMOTE MONITORING, VIEWING AND UPDATING OF PATIENT RECORDS

(75) Inventor: Hesham Soliman, Melbourne (AU)

(73) Assignee: Elevate Technologies Pty Ltd., Melbourne (AU)

( * ) Notice: Subject to any disclaimer, the term of this patent is extended or adjusted under 35 U.S.C. 154(b) by 0 days.

(21) Appl. No.: 13/154,651

(22) Filed: Jun. 7, 2011

(65) Prior Publication Data
US 2011/0234409 A1 Sep. 29, 2011

Related U.S. Application Data

(63) Continuation of application No. 12/269,162, filed on Nov. 12, 2008, now abandoned.

(60) Provisional application No. 60/987,563, filed on Nov. 13, 2007.

(51) Int. Cl.
G08B 1/08 (2006.01)
(52) U.S. Cl. ................................ 340/539.12; 340/573.1
(58) Field of Classification Search ............. 340/539.12, 340/573.1; 370/390, 401; 705/3; 709/219; 382/128; 702/188, 182
See application file for complete search history.

(56) References Cited

U.S. PATENT DOCUMENTS

| 7,138,902 B2 | 11/2006 | Menard |
| 7,156,809 B2 | 1/2007 | Quy |
| 7,252,636 B2 | 8/2007 | Brown |
| 7,301,451 B2* | 11/2007 | Hastings .................. 340/539.12 |
| 7,344,496 B2* | 3/2008 | Iliff .............................. 600/300 |
| 7,761,261 B2 | 7/2010 | Shmueli et al. |
| 7,777,622 B2 | 8/2010 | Baldus et al. |
| 2002/0118112 A1* | 8/2002 | Lang .......................... 340/573.1 |
| 2004/0054760 A1 | 3/2004 | Ewing et al. |
| 2007/0150480 A1 | 6/2007 | Hwang et al. |
| 2008/0059239 A1* | 3/2008 | Gerst et al. ....................... 705/3 |
| 2009/0058635 A1 | 3/2009 | LaLonde et al. |

* cited by examiner

*Primary Examiner* — Toan N Pham
(74) *Attorney, Agent, or Firm* — Crowell & Moring LLP

(57) ABSTRACT

Systems and methods of providing telemedicine services are provided. A system can include a medical device that obtains diagnostic information, a gateway device coupled to the medical device, an application server coupled to the gateway device via wired and wireless networks, a database coupled to the application server, the database storing the diagnostic information, and an analyzing device coupled to the database, the analyzing device analyzes records in the database to identify diagnostic information that exceeds predefined thresholds.

14 Claims, 10 Drawing Sheets

TELEMEDICINE APPLICATION FOR REMOTE MONITORING, VIEWING AND UPDATING OF PATIENT RECORDS

CROSS-REFERENCE TO RELATED APPLICATIONS

The present application is a continuation of U.S. patent application Ser. No. 12/269,162, filed Nov. 12, 2008, which claims priority under 35 U.S.C. §119 to U.S. Provisional Application No. 60/987,563, filed Nov. 13, 2007, the entire disclosure of which is herein expressly incorporated by reference. The present application is related to U.S. patent application Ser. No. 12/110,471, filed Apr. 28, 2008, the entire disclosure of which is herein expressly incorporated by reference.

BACKGROUND OF THE INVENTION

A number of factors are driving the health care and wellness industries to move towards comprehensive support of dynamic monitoring of patients and updating their personal records. This new approach to health care, sometimes coined e-health is driven by the need to reduce the cost of patient treatment and the inefficiencies associated with non-critical patients occupying scarce health care resources like hospital beds and nursing among others. The need for e-health is made more urgent by the ageing population in most industrialized countries.

Electronic transfer of medical records is currently used in hospitals around the world. The Digital Image and Communications in Medicine (DICOM) standard was developed to transfer images and associated patient details between an imaging device (e.g. Ultrasound imaging) and a database. The Health Level 7 standard was developed to track the accounting and visitation records for patients. Other software products are currently used by family doctors to store patient records on their computers. However, with the exception of imaging data, the vast majority of information included in patient records is entered manually. Doctors' and nurses' handwritten notes are often scanned and stored in the patient record.

SUMMARY OF THE INVENTION

A number of medical and wellness devices are currently used by medical practitioners and end users to monitor various bodily functions, for example, blood sugar levels, blood pressure, oxygen concentration in the blood stream, heart rate, etc. There is a clear need for the automation of the process of recording medical information measured by such devices and others.

On the other hand, there are strict requirements for the mechanisms that may be used for recording such sensitive information. For example, the mechanisms used must be secure, reliable and in many cases, timely. Sharing patient information with third parties must be done based on strict authorization. Storage of such information must be secure. Finally, a number of performance-related requirements exist if this information is transferred over a wireless system. Efficiency of the information transfer is necessary in order to appropriately utilize the expensive wireless resources. Depending on the capabilities of the wireless device used and the service being provided, other information associated with the user may be necessary, like the user's location and the type of wireless gateway device being used to relay the information from the medical device to the remote server on the Internet. Several other features associated with the authorization of third parties may be needed.

Exemplary embodiments of the present invention are directed to remotely transferring medical information and updating a patient's record. The present invention is not limited to the health care industry, but it is equally applicable to the wellness industry where users are not sick, but are monitoring their general health, exercise routines or nutrition.

An exemplary method for a medical device involves obtaining diagnostic information, discovering a gateway device, establishing a connection with the gateway device, establishing a session with the gateway device, and transferring, by the medical device, the diagnostic information to the gateway device.

An exemplary system includes a medical device that obtains diagnostic information, a gateway device coupled to the medical device, an application server coupled to the gateway device via wired and wireless networks, a database coupled to the application server, the database storing the diagnostic information, and an analyzing device coupled to the database, the analyzing device analyzes records in the database to identify diagnostic information that exceeds predefined thresholds.

BRIEF DESCRIPTION OF THE DRAWING FIGURES

Other objects, advantages and novel features of the present invention will become apparent from the following detailed description of the invention when considered in conjunction with the accompanying drawings.

DETAILED DESCRIPTION OF THE PREFERRED EMBODIMENTS

Figure 1:
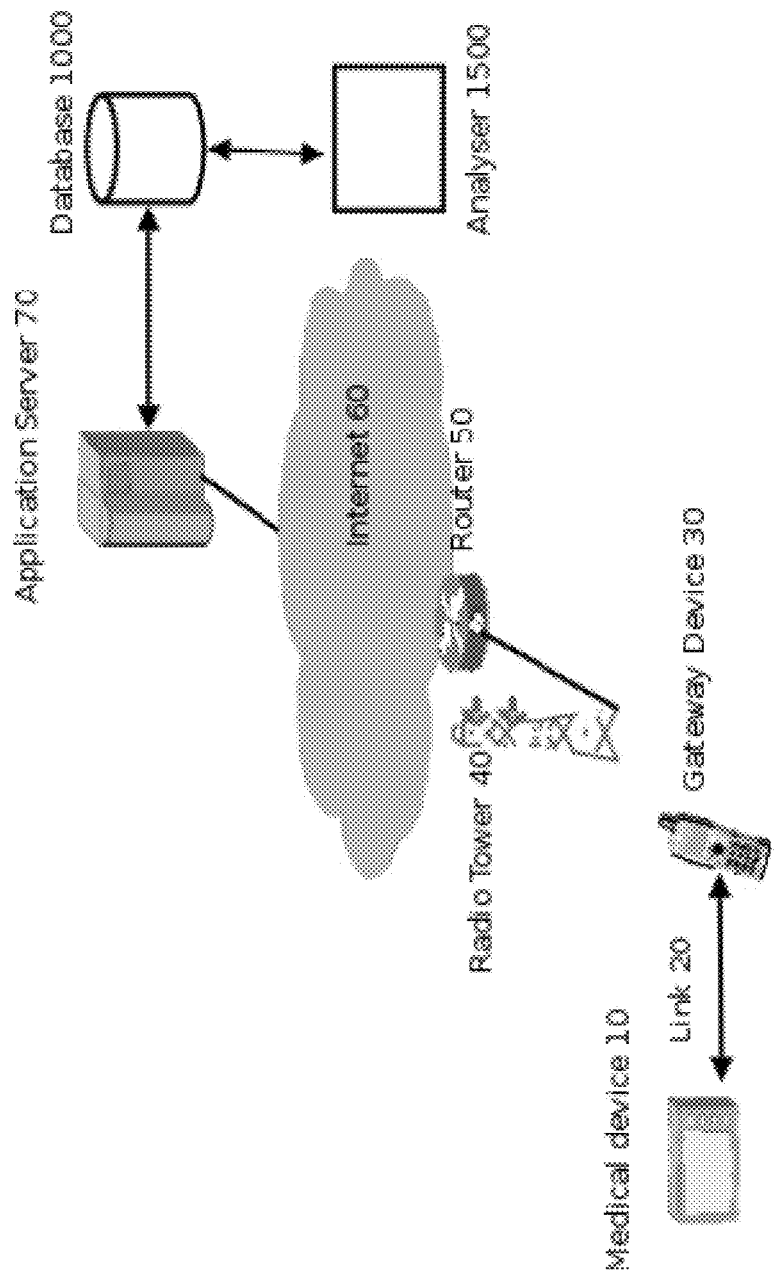
FIG. 1 is a block diagram illustrating an exemplary architecture in accordance with the present invention.

FIG. 1 illustrates the overall system architecture. The system includes medical device 10 coupled by link 20 to gateway device 30. Medical device 10 comprises hardware and/or software that perform functions related to health care, wellness or nutrition. The device measures biological information about a human or an animal and sends such information out to an application relay function in gateway device 30 via link 20.

Link 20 is a wired or wireless link that connects medical device 10 to gateway device 30. Examples of such link include, but not limited to, Infra-red, Bluetooth, Universal Serial Bus (USB), ethernet, or Wireless Local Area Network (WLAN). Medical device 10 and gateway device 30 may be collocated in the same device, in which case the link 20 is represented by the hardware and software internally allowing those two entities to communicate.

Gateway device 30 comprises software and hardware components that allow it to communicate, through wired or wireless links, to other devices on the Internet. This device connects medical device 10 to a remote application server 70 using link 20 to a radio antenna 40 connected to Internet 60. The gateway device also includes the application relay which negotiates the session to the remote application server 70 in order to send information that was earlier sent from medical device 10 or information generated by the application on the gateway device. Gateway device 30 may be connected to the Internet 60 through a wireless network comprising a radio tower 40 and one or many routers 50. References herein to gateway device 30 in signalling exchanges as a single entity includes the software components inside gateway device 30 that initiates such messages.

Application server 70 is responsible for receiving and storing information from gateway device 30, which either originated from medical device 10 or gateway device 30. The application server also manages the authorization of third parties to view, update, or modify a record. Furthermore, the server is responsible for the management of a session between the server and gateway device 30, which includes the management of user authentication, authorization, access rights, flow control of data, user profile, among other factors related to a user's subscription or ongoing data transfer. Storage and retrieval of user records stored in database 1000 is controlled by application server 70.

Database 1000 stores the user's records. Each record is owned by a user, hereafter referred to as the record owner. The database 1000 is populated by application server 70. The database may contain intelligence that allows it to search, categorise and manipulate entries for statistical purposes.

Analyser module 1500 is coupled to database 1000, and searches through the different records in order to look for abnormalities that can be highlighted to a user viewing such records. This includes looking for measurements that are out of normal ranges based on age, race, and sex of a patient. Entries outside normal ranges may be highlighted for better viewing or can be raised as an alert for the record owner and nominated third parties (e.g. family members, health care practitioners, and so on). Furthermore, such alerts, if they cross predefined thresholds, can be used to contact emergency services on behalf of the record owner. Predefined thresholds for different actions can be configured on a per-user basis. Thus, for example, if information provided by medical device 10 to database 1000 indicates an abnormal heart rate, blood glucose level, etc., analyzer 1500 can identify the abnormality and notify a doctor, hospital and/or ambulance service.

Figure 2:
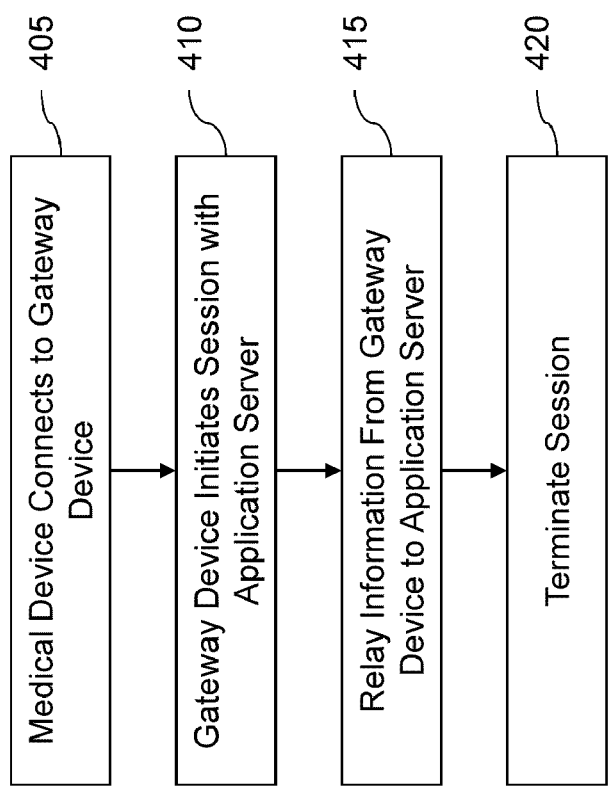
FIG. 2 is a flow diagram of an exemplary method in accordance with the present invention.

FIG. 2 illustrates an exemplary method in accordance with the present invention. Medical device 10 connects to gateway device 30 via link 20 (step 405). During such connection the application generating the information to be sent on medical device 10 announces its properties and identification to the application relaying the information on gateway device 30. In addition, other data pertaining to the type of information being sent and its requirements can be exchanged. Following a successful connection establishment, the application on gateway device 30 initiates a session with application server 70 (step 410). During the initiation, the application performs the necessary security procedures for authentication and authorization. Furthermore, the application on gateway device 30 can exchange information with application server 70 about the type of data being exchanged and its requirements. This may result in application server 70 commanding the application on gateway device 30 to encode the information in a particular manner.

Following a successful session establishment between gateway device 30 and application server 70, information can be relayed from gateway device 30 to application server 70 (step 415). Such information includes data received from medical device 10, as well as, signalling information from gateway device 30 to application server 70. Information can also be sent from application server 70 to medical device 10 via gateway device 30. After information has been exchanged between application server 70 and medical device 10, the session and connection can be terminated (step 420).

As discussed above, medical device 10 and gateway device 30 may be two separate physical devices or collocated within the same physical device. In either case communication between those devices involves connection establishment and data transfer steps. The connection establishment step involves the application on gateway device 30 discovering its peer on medical device 10 and setting up a session between the two peers. In doing so, the application on gateway device 30 needs to first discover its peer, discover its peer's capabilities, then set up a session. The session set up involves exchanging security credentials and the communication port. A communication port may be a logical port on each communicating device, an internet API based socket or any other software module responsible for sending and receiving traffic between the peers. The data transfer step data involves an exchange of data between the two peers. The data encoding and transmission behaviour is exchanged during the discovery and session set-up phases.

Figures 3, 4:
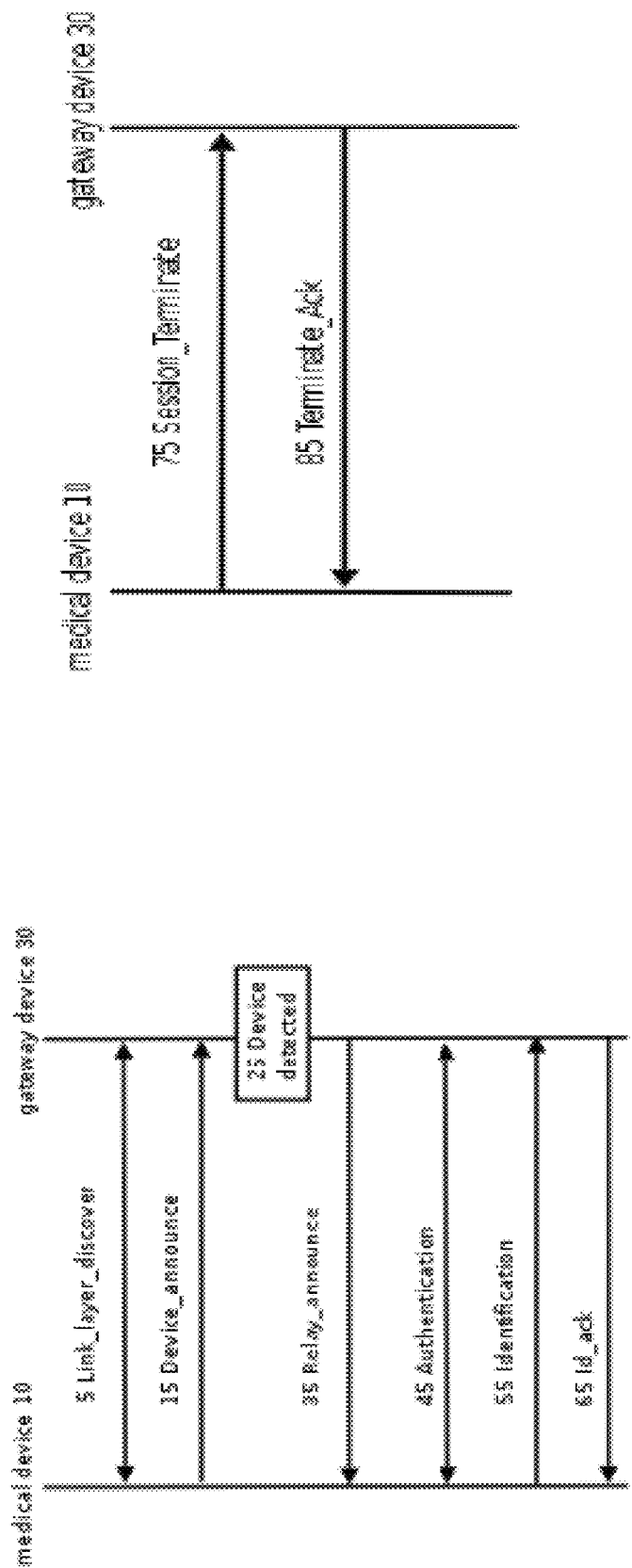
FIG. 3 is a flow diagram of an exemplary method for connection establishment in accordance with the present invention.
FIGS. 4 and 5 are flow diagrams of exemplary methods for session termination in accordance with the present invention.

FIG. 3 illustrates the message flow for peer discovery and connection establishment between the application on gateway device 30 and its peer on medical device 10. The Link_layer_discover 5 message exchange allows the two devices to discover each other's link layer information, such as the link layer address or hardware identification. This message would only take place on the link layer, directly between the two devices if they were sharing the same link or transparently bridged to appear to share the same link. Some link layers (e.g. Bluetooth links) allow for a more sophisticated exchange of information on the link layer. For instance, the Service Discovery protocol (SDP) in Bluetooth allows devices to discover services supported by their peers. For such links, we introduce a new identifier to indicate the support of health services, for instance, the term "vhealth" can be used by medical device 10 to announce that it runs medical or wellness applications. Upon the exchange of link layer discovery and connection information, both devices become aware of each other's link layer details and can send information on that level. Note that as a part of this step, some IP layer messaging in order to discover or configure IP addresses can be exchanged.

The Device_announce 15 message, allows medical device 10 to announce some of the capabilities that are needed in order for the two applications to start communicating. This message contains, at least, the IP address of the device, and types of medical applications supported by the device.

In one aspect of this invention, this message is sent on the IP layer. In this case, this message can be encoded as a new Neighbour Discovery option (RFC 4861) for IPv6, or a new Address Resolution Protocol (ARP) parameter for IPv4. On point-to-point links, the message can be unicast to the gateway device 30. However, on shared links, the message should be multi-cast to several nodes on that link. In one aspect of this invention a unique link-local multicast group is used for medical applications. In another aspect of this invention a unique site-local or organisation-local address is used for medical applications. In another aspect of this invention the message is sent to the Well-Known All nodes multicast IP address in IPv6 or broadcast to all nodes on IPv4 links.

In another aspect of this invention this message is sent by the application layer. Where TCP/IP is used for this communication, the application on medical device 10 can send this message to a reserved, well-known port, or a preconfigured port for the application relay on gateway device 30. If TCP/IP is not used for this communication, applications on medical device 10 can send this message to a negotiated or preconfigured communication port. In yet another aspect of this invention this message can be added to link layer exchanges during the link layer discovery phase or after configuring an IP address for communication. After processing message 15, gateway device 30 detects medical device 10 and its application capabilities as illustrated by the device detected block 25.

After discovering medical device 10 on the link layer and potentially the IP or application layers, the application relay on gateway device 30 announces itself in the Relay_announce message 35 sent to the medical device. This message serves to acknowledge the reception of message 15 and announce the application relay's capabilities to medical device 10. This message includes, at least, the application relay's IP address and port. The application relay's IP address is one of the IP addresses configured on gateway device 30. If no IP address is configured, the link layer and communication port information should be announced instead. The application relay's port identifies the communication port, represented by name or number, that the application relay expects its peer on medical device 10 to send its information.

On point-to-point links, the message is sent directly from gateway device 30 to medical device 10. However, on shared links, the message may be sent gratuitously to a unique multicast group that includes all medical devices. The scope of such group may be link-local, site or organization-local. However, when responding to a specific medical application device, the application relay on gateway device 30 may unicast this message to the medical device in order to include the acknowledgement information for the Device_announce 15 message. This message may be sent on the IP layer (for both IPv4 and IPv6), the application layer, or the link layer.

In the Authentication step 45 mutual authentication between the two applications takes place. In one aspect of this invention, mutual authentication can be based on preconfigured credentials in medical device 10 and gateway device 30. In another aspect of this invention, mutual authentication can be performed based on Public keys configured in both applications and exchanged during message exchange 45.

The Identification message 55 is then sent from the application running on medical device 10 to its peer application relay running on gateway device 30. The message includes, at least, the following information:

The application identifier field, which contains information that identifies the application. The information included in this field would contain at least the following:
  Application type parameter, which indicates the functions supported by the application. For instance, an application may be used to measure an electro-cardiogram, heart rate, kidney functions, and so on. Each application is allocated a name or a number that can be used by the receiver to detect the type of application.
  Application vendor parameter, which indicates the vendor of the application. Different vendors may have different formats for the data.
  Data encoding parameter, which indicates the data encoding scheme. For instance, the data may be sent in binary format, text format, XML, and so on.
  Data compression parameter, which indicates whether a compression mechanism, if any, is used to send the data, and if it is, the mechanism is identified.
  Quality of Service (QoS) information field, which includes information about the traffic behavior sent by the application. This includes expected packet inter-arrival, delay tolerance, reliability requirements, packet ordering requirements, and so on.
The software version supported by the application. This information allows the relay agent to learn the software supported by medical device 10 application.
The data encoding formats supported by the application on the medical device.
Compression mechanisms supported by the application running on medical device 10.

The Id_ack 65 message is sent from the application relay running on gateway device 30 to medical device 10. This message acknowledges the reception of the identification message and informs the application on medical device 10 whether a session can be established. If a session can be established, this message contains a session identifier that can be used by the application running on medical device 10 during data transfer. Moreover, as described below, additional information about attributes for the data flow is included in this message. The session identifier can be included in every message sent from the application on medical device 10 to the application relay on gateway device 30 to allow the application relay to identify the session associated with the data transmitted. The session identifier can also be used as a look-up key when data between the two devices is encrypted on the application layer. This message can be authenticated and encrypted based on the keying material derived after the authentication message exchange 45. Hence, this message contains, at least, the following information:

Acknowledgement for receiving the Identification message 55.
If session establishment is successful, a session identifier is included. The session identifier may be a 64-bit number. This number may be randomly generated or selected by the application relay by other means.
If session establishment failed, an appropriate error code is included.

Authentication and encryption data used to authenticate this message by the receiver.

Selection of the application relay's preferred data encoding format for data sent by the application on medical device 10. This is needed when the application on the medical device supports multiple formats while the application relay prefers a specific format or supports a smaller number of formats.

Compression requirements parameter, which informs the application on medical device 10 whether compression should be used and if it is, what compression mechanism should be used.

Now that the discovery and connection establishment processes has been presented, the processes associated with data transmission between the application running on medical device 10 and the relay application on gateway device 30 is discussed in detail below.

Based on the data format preferences exchanged between medical device 10 and gateway device 30 during the discovery process encompassing the Identification 55 and Id_ack 65 messages, gateway device 30 commands medical device 10 to use one of its preferred formats for data transfer. After a session is established, medical device 10 can start transmitting information to gateway device 30. Regardless of the data format, each packet contains the following information:

Source address.

Destination address.

Session identifier.

A message identifier parameter that uniquely identifies a message within a session. This can be represented by a large number used as a counter.

Communication ports.

The application identifier (optional).

Amount of information waiting for transmission.

An urgent alert parameter that alerts the application relay that there may be a medical emergency that needs attention based on the measurements performed. This parameter need not hold binary values. There may be different levels of urgency that need to be communicated. A device may be running out of battery power and needs to send data as soon as possible. Similarly, a device may be lacking other resources and therefore needs to send data to free some of its resources. Hence, this parameter may hold various values depending on the level of urgency experienced.

A data parameter that contains information generated by medical device 10.

Exemplary embodiments of the present invention employ signalling messages exchanged between the application on medical device 10 and gateway device 30 to convey information about the data exchanged or the session as a whole.

Figure 5:
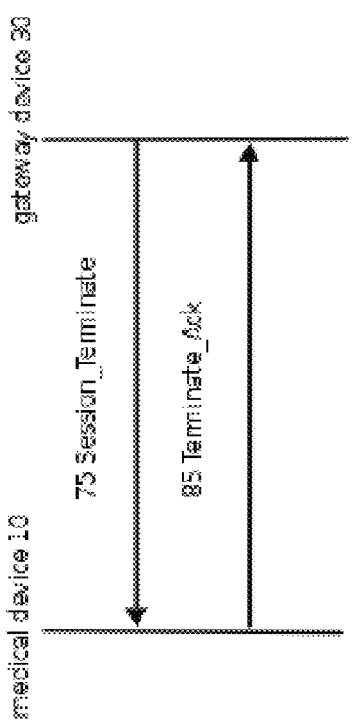

Session termination may take place due to several reasons, including lack of resources, lack of data to send, errors in transmission, and so on. Either the application on medical device 10 or gateway device 30 can terminate the session at any time. FIGS. 4 and 5 illustrate how session termination can take place when initiated by either end of the communication.

When terminating the session, the application on medical device 10 sends the Session_Terminate 75 message to the application relay on gateway device 30. The Session_Terminate 75 message contains, at least, the session identifier and reason for termination. The session identifier parameter is the same parameter provided by the application relay when the session was established. This parameter is used by the receiver to identify the session being terminated and the resources associated with such session. The reason parameter indicates the reason for terminating the session. There may be several reasons for the termination including: idle timeout, no measurements being done, lack of resources, communication errors, and so on.

After sending this message, the sender may maintain some of the resources associated with the session in order to identify the acknowledgement message from the receiver. For instance, the session identifier may not be deleted until an acknowledgement is received or a timeout takes place.

Upon receiving this message, the receiver identifies the session and its resources. The receiver then takes the necessary steps to terminate the session and free its resources. Following that, the receiver then sends the Terminate_Ack message 85 to the sender. The Terminate_Ack message 85 includes the session identifier and status parameters. The session identifier parameter is the same parameter included in the Session_Terminate message 75. The status parameter indicates the success or failure of the operation and reasons for failure. If the Terminate_Ack message 85 is received indicating failure at the other end, the receiver of such message may ignore such failure and remove all resources associated with the session.

FIG. 5 illustrates how a session can be terminated by the application relay on gateway device 30. The same steps described above would apply to the termination initiated by gateway device 30.

In some cases, mostly due to erroneous state management in one of the communicating entities, a peer may send a message that contains an unrecognisable session identifier. This situation may also happen if one of the peers lost state due to a reboot or corruption of its memory. In this case, the receiver sends the "Session_unknown" message 90 back to the sender. This message contains the session identifier received. Upon receiving such message, the sender of the original message may remove the session corresponding to that message identifier in order to synchronise states with its peer. This mechanism may be used with a reserved session identifier value to indicate to a peer that the device has lost all states with such peer. Hence, this message can be used by either the medical application or the application relay to communicate general loss of state to its peer.

Figure 6:
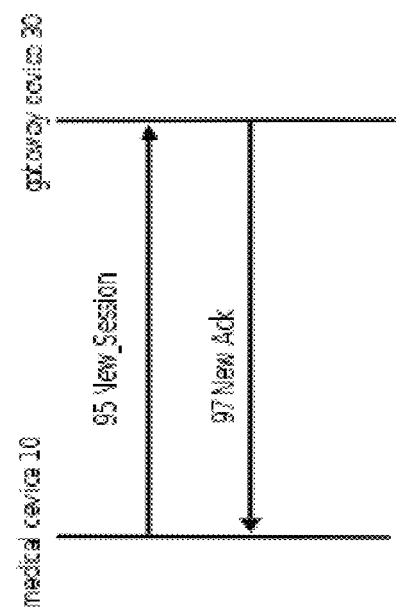
FIG. 6 is a flow diagram of an exemplary method for session establishment in accordance with the present invention.

The medical application running on medical device 10 may at any time need to create a new session. For instance, this can be useful if such application sends several independent streams of traffic that can be separated under different sessions. In order to do that, the message exchange in FIG. 6 is performed, which involves sending a New_Session message 95 from medical device 10 to gateway device 30 and receiving a New_Ack response by medical device 10 from gateway device 30. The New_Session message 95 may also be sent from gateway device 30 to medical device 10. The New_Session message 95 requests a new session identifier from the application relay. The message includes, at least, the following parameters:

Source and destination addresses.

Source and destination communication ports.

Session identifier parameter, which is the new session identifier requested by the sender. It includes a suggested session identifier.

Application identifier parameter, which includes the application identifier previously included in the Identification message 55.

Upon receiving this message, the recipient parses the message to ensure all fields are formatted correctly. If there is no conflict between the suggested session identifier in the message and an existing session identifier, the suggested identifier is accepted. Otherwise, the message is rejected with a suitable error code in the New_Ack message 97. The New_Ack message 97 includes, at least the following information:
- Source and destination addresses.
- Source and destination communication ports.
- Result parameter, which indicates success or failure of the operation. Different error codes can be used to indicate reasons for failure.

The protocol between the medical device application and the application relay on gateway device 30 can use a reliable mode of data transfer by using acknowledgement messages. The acknowledgement message can be sent from either the medical application or the application relay in order to confirm reception of one or more data or signalling messages. The acknowledgement message can also act as a negative acknowledgement by including one or more message that was not received. The acknowledgement message includes, at least, the following information:
- Source and destination addresses
- Source and destination communication ports
- Session Identifier
- Message identifier
- Acknowledgement type parameter, which indicates whether a positive or negative acknowledgement is included in this message.
- Message identifiers parameter, which includes on or more message identifiers that are being positively or negatively acknowledged.
- Transmission Window field, which indicates the number of bytes that the sender can receive without sending back an acknowledgement message.

Flow control can be critical for cases where a large amount of information is sent from the medical application running on medical device 10 to the application relay running on gateway device 30. It is important for the application relay to regulate the flow of traffic to avoid congestion. The Transmission Control Protocol (TCP) provides native flow control mechanisms. However, TCP may or may not be used between the two applications. Furthermore, this invention allows more than one device to be connected to the gateway device. Hence, it is critical that application relay on gateway device 30 prioritizes and regulates flow control from different devices.

In order to regulate the flow from a single medical application, the application relay includes the Transmission Window parameter in its Acknowledgement messages sent to the medical application. This Transmission Window size informs the medical application that it can transmit the included number of bytes without waiting for an acknowledgement. After sending that number of bytes, the medical application waits for an acknowledgement message. If that acknowledgement message only contains the last received message, it is an indication to the medical application that all messages sent since the last acknowledgement was sent. Upon receiving this, the medical application can reset the window size and start transmitting new data.

Figures 7, 8:
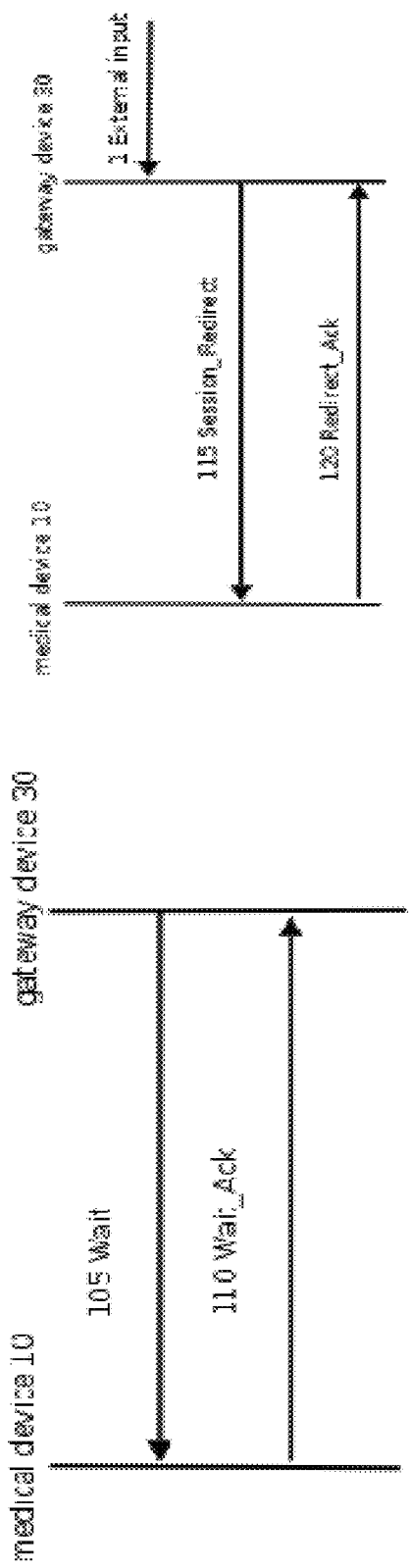
FIG. 7 is a flow diagram of an exemplary method for exchange a wait message in accordance with the present invention.
FIG. 8 is a flow diagram of an exemplary method for session redirection in accordance with the present invention.

FIG. 7 illustrates an exemplary message exchange used to slow down or temporarily stop the information transfer between the medical application and its peer, the application relay. The Wait message 105 is sent from the application relay to the medical application on medical device 10. The Wait message 105 commands the medical application on medical device 10 to reduce the rate of information transmission or stop it for a period of time. Hence, the message contains the following parameters:
- Source and destination addresses.
- Source and destination communication ports.
- Session identifier.
- Message identifier.
- Transmission window size parameter, which includes the new transmission window for future messages. A transmission window size of zero indicates that the medical application should stop sending messages and buffer information until a larger value is sent in the transmission window parameter. A new Wait message 105 or an Acknowledgement message can overwrite this transmission window by including a higher or lower value.

The Wait_Ack message 110 is sent from the medical application on medical device 10 to the application relay on gateway device 30. The purpose of this message is to acknowledge the receipt of the Wait message 105. If the medical application is requested to stop transmission for a period of time (by including a value of zero in the transmission window parameter) the medical application may choose to send a buffer-size parameter in the Wait_Ack message 110, which indicates how long it can buffer packets. The buffer-size parameter can be represented by time units or number of bytes. Hence, the Wait_Ack message 110 includes, at least, the following parameters:
- Source and destination addresses.
- Source and destination communication ports.
- Session identifier.
- Message identifier.
- Buffer-size.

The application relay running on gateway device 30 may command the medical application on medical device 10 to redirect one or more sessions to a new peer using the session redirection exchange illustrated in FIG. 8. This may be done for load-balancing, to obtain better access to the Internet, or to send session information to another entity that needs it more urgently (e.g. a physician, paramedic, and so on). The redirection command may be triggered by a command sent to the application relay from a remote entity or due to manual intervention by the user.

Based on, optionally, an external input 1, the application relay on gateway device 30 may decide to send the Session_Redirect message 115 to the medical application on medical device 10, with which a session already exists. The Session_Redirect message (115) contains, at least, the following information:
- Source and destination addresses.
- Source and destination communication ports.
- Session identifier.
- Message identifier.
- New peer parameter, which includes the reachability information of the peer that the medical application is being redirected to. This may include an address and communication ports.
- Redirected sessions parameter, which includes the session identifiers for those sessions that need to be redirected to the new peer.
- Authentication credentials for the new peer parameter, which is optional, and includes the credentials of the new peer of the medical application on medical device 10.

Upon receiving the Session_Redirect message 115, the medical application checks the session identifier parameter. If the session identifier does not match an existing session, an error code can be included in the Redirect_Ack 120 message. Alternatively, the medical application may send a Session-unknown 90 message including the session identifier. However, if the session identifier were valid, the medical application starts the authentication process with the new peer. If the peer's full reachability information were not provided the medical application may have to start the discovery phase presented in FIG. 3.

Following the processing of the Session_Redirect message 115, the medical application sends the Redirect_Ack 120 message. This message includes at least the following information:
Source and destination addresses.
Source and destination communication ports.
Session identifier.
Message identifier.
Result field, which indicates whether the redirection of the session was successful or not and the reasons given for failure.

If the redirection was not successful the application relay may command the medical application to try again, or, alternatively, continue receiving traffic in this session. If the redirection was successful, the session is closed.

Figure 9:
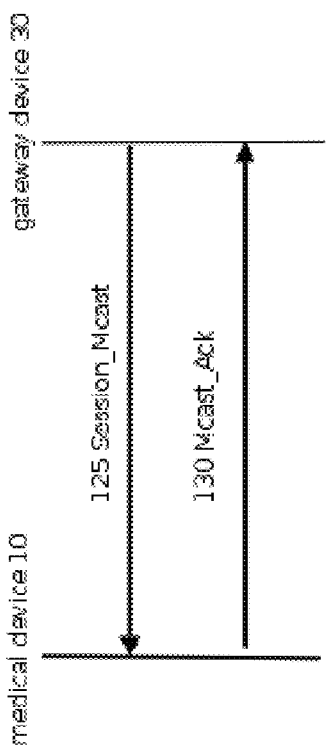
FIG. 9 is a flow diagram of an exemplary method for session multicasting in accordance with the present invention.

The application relay on gateway device 30 may command the medical application on medical device 10 to multicast one or more sessions to several peers, which may include the application relay sending this message. Such data duplication can be useful when several entities need to store or observe particular information coming from the medical application on medical device 10. Like the Session_Redirect message, session multicasting can take place as a result of a command from a remote server or manual intervention by the user. In order to order session multicast, the application relay on gateway device 30 sends the Session_Mcast message 125 as shown in FIG. 9.

The Session_Mcast message 125 contains at least the following information:
Source and destination addresses.
Source and destination communication ports.
Session identifier.
Message identifier.
New peers parameter, which provides reachability information for the peers that the medical application needs to multicast sessions to. This may include addresses and communication ports. The application relay sending this message may also include its own reachability information to indicate that it should continue to receive traffic for the multicast session.
Session identifiers parameter, which includes one or more session identifier that identifies session that need to be multicast to the new peers. An implementation may choose to only include one session identifier per Session_Mcast message. In this case, if multiple sessions need to be multicast, multiple Session_Mcast messages will need to be sent, each as part of the session being multicast.
Authentication credentials for new peer's parameter, which includes multiple authentication credentials, one for each peer. This parameter is optional.

Upon receiving the Session_Redirect message 125, the medical application on medical device 10 checks the session identifier parameter. If the session identifier does not match an existing session, an error code can be included in the Mcast_Ack 130 message. Alternatively, the medical application may send a Session_unknown 90 message including the session identifier. However, if the session identifier were valid, the medical application starts the authentication process with the new peers. If the peers' full reachability information were not provided the medical application may have to start the discovery phase presented in FIG. 3.

Following the processing of the Session_Mcast message 125, the medical application sends the Mcast_Ack 130 message. This message includes at least the following information:
Source and destination addresses.
Source and destination communication ports.
Session identifier.
Message identifier.
Result parameter, which contains the result of the operation and indicates success or failure. If the operation failed for some peers, such peers would be included in this message. If the operation failed for entire sessions, those session identifiers would be included.

Now that the messaging between the medical device and gateway has been described, the messaging between gateway 30 and application server 70 will be discussed. Messages exchanged between those two entities can be divided into two categories: 1) Signalling messages and 2) data messages. Signalling messages deal with session initiation, which includes server discovery, session control, and session maintenance. Data messages are packets that include data exchanged between gateway device 30 and application server 70.

Figure 10:
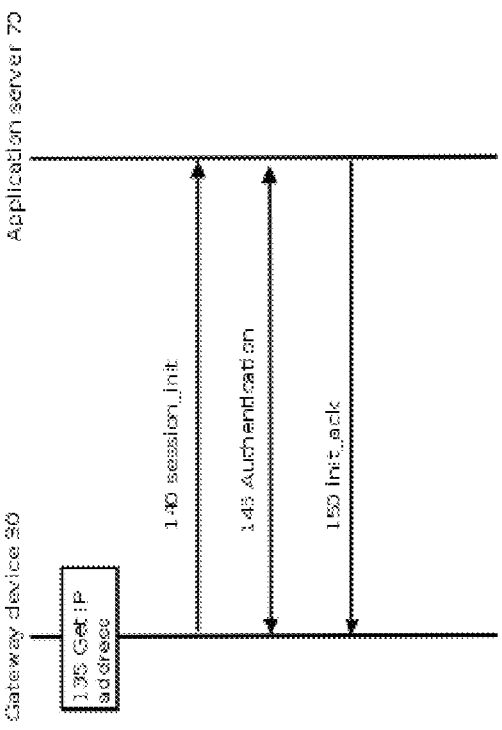
FIG. 10 is a flow diagram of an exemplary method for session establishment in accordance with the present invention.

Initially, gateway 30 employs a server discovery process to discover the address of application server 70 and initiate a new session. This process is illustrated in FIG. 10. Gateway device 30 starts the discovery process by obtaining the IP address of application server 70 as represented by block 135. In one aspect of this invention, this can be done through manually configuring the IP address in gateway device 30. In another aspect of this invention the IP address can be obtained dynamically using the Domain Name System (DNS) (RFC 1033, RFC 1034, RFC 1035) or the Dynamic Host Configuration Protocol for IPv4 or IPv6 (RFC 2131 and RFC 3315).

After the IP address of application server is obtained, the application on gateway device 30 sends a session_init message 140. This message contains, at least, the following parameters:
The source and destination addresses
The source and destination communication port numbers. This is typically the port number identifying the communication sockets when using the TCP/IP communication suite.
The user's identifier. This parameter is either a unique alphanumeric string or number that identifies the user that owns an account on application server 70.

This message starts the authentication process 145 where both gateway device 30 and application server 70 authenticate each other. After a successful authentication phase, the application server sends the init_ack 150 message. This message is authenticated based on the credentials derived from the authentication phase 145 and contains, at least, the following information:
The source and destination addresses
The source and destination communication port numbers. This is typically the port number identifying the communication sockets when using the TCP/IP communication suite.
The user's identifier. This parameter is either a unique alphanumeric string or number that identifies the user that owns an account on application server 70.
The session identifier, which is a unique number chosen by application server 70.
Record indices. This is an optional parameter sent from application server 70 to gateway device 30 to provide it with the indices used by the server to identify parts of the user's record. These indices can be used later by gateway device 30 to create or update entries in the user's record. Indices are essential to inform the server where such entries should be stored (i.e. under what category).

Application server's address parameter, which may include a different address from that used by the sender of this message. Essentially, this parameter can be used by the sender to redirect the application on gateway device 30, to another server. This may be done for load sharing, or to separate the servers handling the signalling messages from those receiving payload data.

Authentication and encryption data. This parameter includes the data needed by the receiver to authenticate and decrypt the message.

Figures 11, 12:
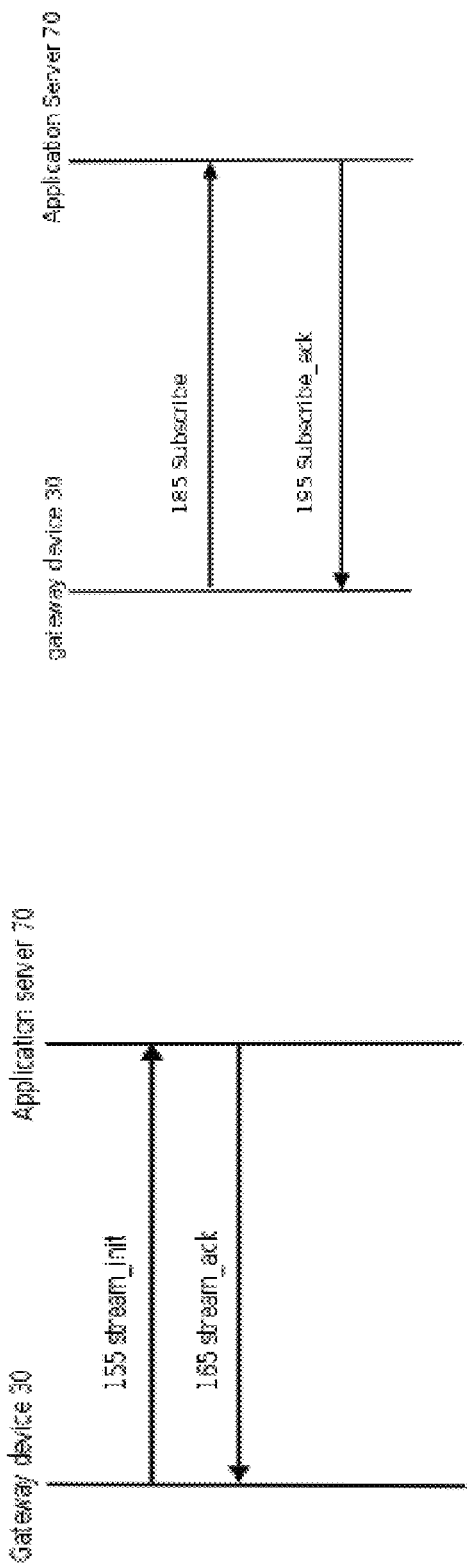
FIG. 11 is a flow diagram of an exemplary method for stream initiation in accordance with the present invention.
FIG. 12 is a flow diagram of an exemplary method for event subscription in accordance with the present invention.

A session may contain one or more streams that correspond to different types of information being exchanged between gateway device 30 and the application server 70. When initiating a new stream, gateway device 30 indicates the type of information intended for such stream by including the application identifier parameter. This parameter allows application server 70 to identify the information and allocate the necessary resources for it. FIG. 11 illustrates the stream initiation process. The application on gateway device 30 sends the stream_init 155 message. This message is authenticated based on the credentials derived from the authentication phase 145. The message contains, at least, the following information:

The source and destination addresses

The source and destination communication port numbers. This is typically the port number identifying the communication sockets when using the TCP/IP communication suite.

The user's identifier parameter, which is either a unique alphanumeric string or number that identifies the user that owns an account on application server 70.

The application identifier. This is the application identifier presented earlier in the Identification message 55.

The payload label parameter, which is optionally included in the message and contains an alphanumeric string that includes the label for the payload information sent in this session. The label may be manually added by the user or automatically generated by the application on gateway device 30. This label can be a readable string that allows users to later distinguish different entries in their records.

The latest version supported by the application on gateway device 30.

Authentication and encryption data.

Upon receiving this message, application server 70 sends the stream_ack 165 message. This message is authenticated by the credentials derived from the authentication phase 145. This message contains, at least, the following information:

The source and destination addresses

The source and destination communication port numbers. This is typically the port number identifying the communication sockets when using the TCP/IP communication suite.

The session identifier.

A stream identifier parameter, which identifies a particular stream within a session. A session may contain one or more streams corresponding to different sets of information being sent by gateway device 30. The stream identifier is then used by gateway device 30 in each payload packet.

The storage identifier parameter, which identifies the part of the user's record where the information needs to be stored. The identification of the part of the user's record that will contain this information may be done manually (by the user) or inferred by the server based on the application identifier information sent in the stream_init 155 message.

Result parameter, which contains the result for the operation which indicates either success or failure and the reason for such failure.

Authentication and encryption data.

Gateway device 30 may at any time subscribe to a particular event. Examples of events include comments that may be added to the profile, messages, alerts of any kind and reminders. In order to subscribe, the gateway device sends a subscription request message 185 to the application server. FIG. 12 illustrates this message exchange. The Subscribe message is sent from the Gateway device to the application server. It contains the following information:

Source and destination addresses

Source and destination communication ports

Session identifier

Event descriptor parameter, which includes either an index to a particular event or a string that describes the event.

Authentication and encryption data.

The application server responds with the Subscribe_Ack 195 message to gateway device 30. This message includes the following information:

Source and destination addresses

Source and destination communication ports

Session identifier

Status parameter, which includes information that indicates success or failure of the operation. In case of failure, reasons are specified.

Authentication and encryption data.

Figure 13:
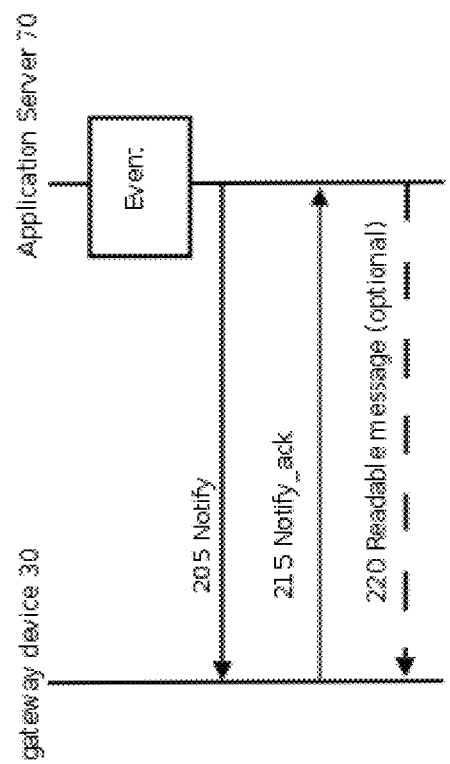
FIG. 13 is a flow diagram of an exemplary method for an event notification process in accordance with the present invention.

When a particular event that the gateway device subscribed to takes place, the application server sends a Notify message. Different events may address different needs. Some events address the user, other address the application software and may be transparent to the user. The application server may send a readable message to the user instead of, or in addition to the Notify message. Examples of readable messages include the Short Message Service (SMS) or electronic mail (e-mail). FIG. 13 illustrates this message exchange. Initially, a Notify message 205 is sent from application server 70 to gateway device 30. This message informs the gateway device that an event, for which the device has subscribed, has taken place. The Notify message contains the following information:

The source and destination addresses

Source and destination communication ports

Session identifier.

Event parameter, which describes the event that took place. This can be done by simply including an index representing the event, user readable text for display.

Authentication and encryption data.

The Gateway device responds to the Notify message 205 with a Notify_ack message 215. The Notify_ack message contains the following information:

The source and destination addresses

Source and destination communication ports

Session identifier.

Status parameter, which indicates success or failure of the operation. Depending on the content of the message, the server may take further action.

Authentication and encryption data.

The application server 70 may send a readable message 220 instead of, or in addition to the Notify message 205. Acknowledgement of such message depends on the protocol being used to send the message.

User records can be retrieved by gateway device 30 or any other viewing device that the user may choose. For simplicity, gateway device 30 is described as the retrieving device. In order to retrieve records, the gateway device needs to request top level indices for the record. This refers to the main sections in the record, each identified with a unique index. The gateway device can then request child records. Child records are subsets of the main sections represented by the top level indices. Each top level index is identified by a name that may be represented as a string. In addition, each entry (including top level and child records) can be associated with a number of attributes that describe the format of the data included in the entry, dates, and other logs associated with such data.

Figure 14:
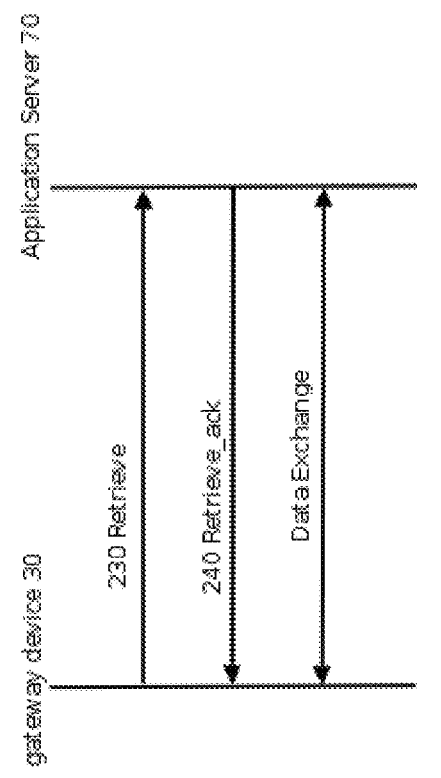
FIG. 14 is a flow diagram of an exemplary method for retrieving data from an application server in accordance with the present invention.

All types of entries can be retrieved from application server 70 using the Retrieve message 230. This message requests one or more entries. The message exchange for retrieving records is illustrated in FIG. 14. The Retrieve message 230 contains the following information:

The source and destination addresses.
The source and destination communication ports.
The session identifier.
The stream identifier.
Data retrieval request parameter, which identifies the data to be retrieved by gateway device 30. This parameter can indicate a request to retrieve a specific entry in the user record, a group of entries (e.g. all parent entries), or all entries in the user's record.
Authentication and encryption data parameter, which includes data that can be used to verify the authenticity of the message and decrypt it.

Upon processing the retrieve message, application server 70 sends the retrieve_ack message 240. This message contains the following information:

The source and destination addresses.
The source and destination communication ports.
The session identifier.
The stream identifier.
Status parameter, which indicates success or failure of the operation.
Entry ports parameter, which informs the gateway device of which entries may need to be retrieved from other communication ports or network addresses. For instance, application server 70 may tell gateway device 30 to retrieve some entries as files, using the file transfer protocol (FTP). In this case, such information would be included in this parameter and the gateway device would then retrieve those entries from the addresses or communication ports provided by application server 70.
Data parameter, which contains some or all of the entries requested by gateway device 30. If the requested entries could not be sent in this message (e.g. too long for one message), then the application server will send them in separate messages. These messages are highlighted by the "Data Exchange" line in FIG. 14.
Authentication and encryption data parameter, which includes data that can be used to verify the authenticity of the message and decrypt it.

After receiving the retrieve_ack 240 message, the gateway device will be able to receive data from the application server. Data transferred between the application on gateway device 30 and application server 70 takes place after a session and a stream are established. Each packet transferred between those two entities contains information about the sender and the receiver, whose IP addresses was conveyed to the application on gateway device 30 during the session establishment process. In addition, each packet contains the session identifier, the stream identifier, and information about the payload contained in the packet. The type of payload can either be inferred from the application identifier exchanged during session establishment or included in each packet. Additionally, the operation required is included in the packet carrying the payload. The operation may request the application server to create a new entry, update an existing entry, or delete and entry. Other operations can be added to the protocol as needed.

The data transferred between the application on gateway device 30 and application server 70 can use any transport protocol mechanism, like the User Datagram Protocol (UDP), the Transmission Control Protocol (TCP) or other transport protocols. A payload data packet contains the following information:

The source and destination addresses.
The source and destination communication ports.
The version of the protocol being used.
The session identifier.
The stream identifier.
Packet identifier parameter, which uniquely identifies a packet within a stream. When combined with the stream identifier it uniquely identifies a packet within a session.
Operation parameter, which indicates the type of operation requested for the payload. For instance, this indicates: create entry, update entry, or delete entry.
Indication of fragmentation parameter, which indicates whether the payload included is a fragment of larger pieces of information, and if so, its order, or that the payload includes all of the data transferred.
Payload Data field, which includes user generated, gateway device generated, or medical device generated data that is transferred to application server 70.
Authentication and encryption data.

Data sent from gateway device 30 or application server 70 is acknowledged by the receiver using the acknowledgement message. This message contains, at least, the following information:

Source and destination addresses.
Source and destination communication ports.
Session identifier.
Stream identifier
Packet identifier.
Acknowledged fragments parameter, which contains one or more fragment numbers that are being acknowledged by the application server. The fragment numbers are obtained from the Indication of fragmentation parameter described above. This parameter may simply contain the last received fragment, which would indicate that every fragment up to the one included in this parameter was received correctly.
Authentication and encryption data.

Figure 15:
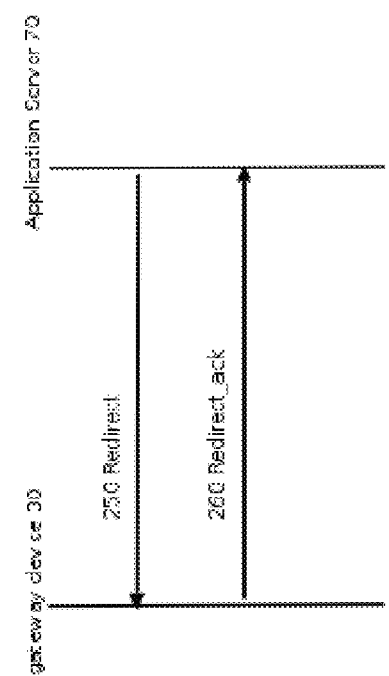
FIG. 15 is a flow diagram of an exemplary method for a redirect process in accordance with the present invention.

The application server 70 can order the client to redirect a session to another server. The redirection may order the application on the gateway device to re-authenticate itself to the new application server, or simply continue transmission provided that authenticated acknowledgements are received from application server 70. Redirection can also be done for a particular request. For instance, the gateway device may request a particular operation that cannot be met by the current application server 70; application server 70 can redirect gateway device 30 to another server that can fulfil its request. However, this does not necessarily mean that future request will automatically go to the new server. Hence, the redirection process can be permanent, or done on a task-by-task basis. The redirection message exchange is illustrated in FIG. 15.

The Redirect message 250 can be sent by either gateway device 30 or application server 70. When this message is sent from application server 70 to gateway device 30 it is based on either an external event, or a request from gateway device 30. The Redirect message contains the following information:

The source and destination addresses.
The source and destination communication ports.
The version of the protocol being used.
The session identifier.
The stream identifier.
Reason parameter, which indicates the reason for the Redirect message. The reason can indicate non-availability of a service, entry retrieval, change in network conditions, and administrative policy among other reasons. This parameter also indicates whether the change is permanent, i.e. redirecting the entire session, the stream, or only for a particular request that can be best met by another server.
Redirection information parameter, which provides the necessary information for the receiver in order to be able to establish a connection with the new entity. Examples of such information include the new entity's IP address, transport protocol (e.g. UDP or TCP) and the port number that should be used. This parameter also indicates whether a new security association needs to be established.
Authentication and encryption data.

After processing the Redirect message 250, the receiver sends the Redirect_ack message 260, which contains the following information:

The source and destination addresses.
The source and destination communication ports.
The version of the protocol being used.
The session identifier.
The stream identifier.
Status parameter, which indicates success or failure of the operation. In case of failure, this parameter indicates the reason for failure.
Authentication and encryption data.

Figure 16:
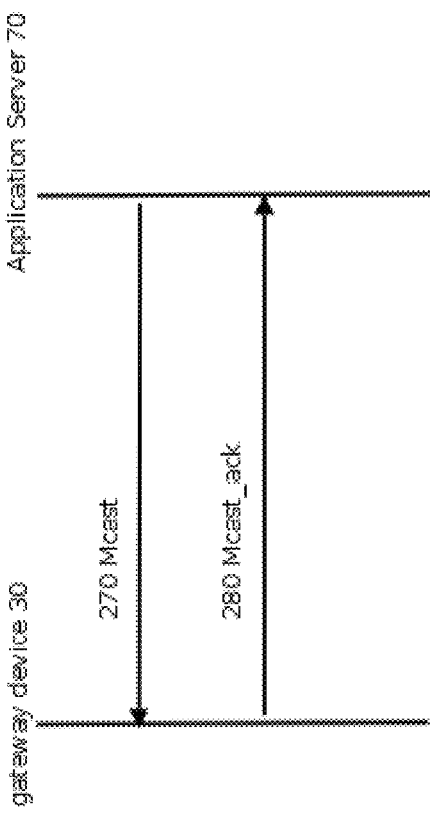
FIG. 16 is a flow diagram of an exemplary method for a multicasting operation in accordance with the present invention.

Session multicasting involves the request from either gateway device 30 or application server 70 for the other end to send the information to multiple entities. The gateway device may request the server to send data to multiple devices, including itself. The same request can come from application server 70 to gateway device 30 in order to allow other entities to receive information. The multicasting request-response process is shown in FIG. 16. For simplicity, we only show the case where the request is made by application server 70. However, the reverse can also be true. The Mcast message 270 contains the following information:

The source and destination addresses.
The source and destination communication ports.
The version of the protocol being used.
The session identifier.
The stream identifier.
Reason parameter, which indicates the reason for the Mcast message. The reason can indicate emergency, multiple viewing devices or administrative policy among other reasons. This parameter also indicates whether the change is permanent, i.e. redirecting the entire session, for this stream, or only for a particular request.
Multicasting information parameter, which provides the necessary information for the receiver in order to be able to establish a connection with the new entities. Examples of this data include the IP address of the new entity, the protocol to be used (e.g. UDP or TCP) and the port numbers. This parameter also indicates whether a new security association needs to be established.
Multicast off parameter, which is used to request that the receiver stop multicasting the session or stream that was being multicast. This parameter is only added when the sender wishes to stop an existing multicast. Stopping a multicast implies that the multicast traffic is unicast to the original receiver before multicasting started.
Authentication and encryption data.

Upon successfully processing the Mcast message 270, the receiver sends the Mcast_ack message 280 to acknowledge reception. The Mcast_ack message 280 contains the following information:

The source and destination addresses.
The source and destination communication ports.
The version of the protocol being used.
The session identifier.
The stream identifier.
Status parameter, which indicates success or failure of the operation. If the operation failed, this parameter would indicate the reason for failure.
Authentication and encryption data.

Figures 17, 18:
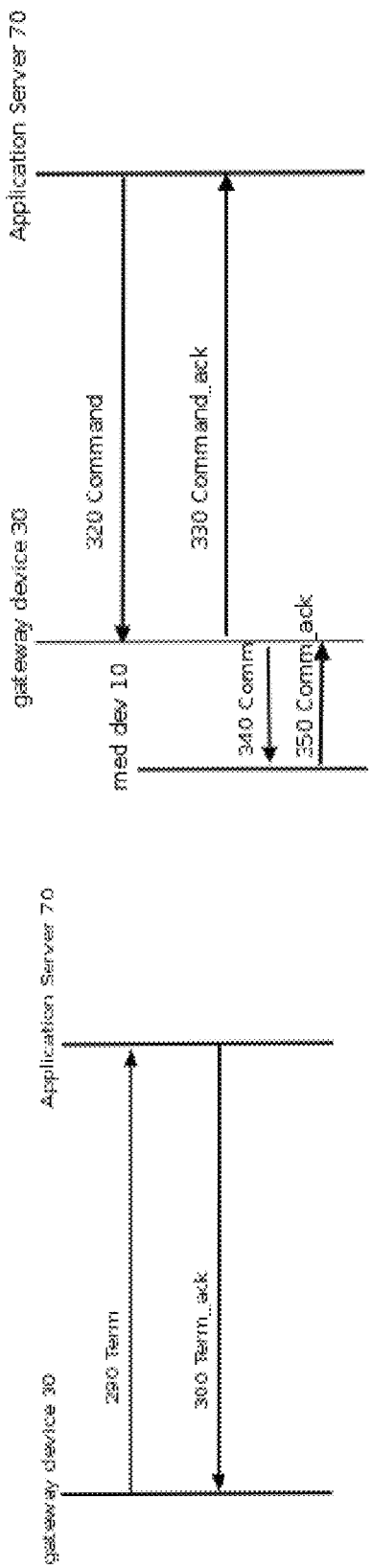
FIG. 17 is a flow diagram of an exemplary method for session termination in accordance with the present invention.
FIG. 18 is a flow diagram of an exemplary method for a command message exchange in accordance with the present invention.

Either gateway device 30 or application server 70 can terminate a session at any time. Session termination implies the termination of all streams within the session. Termination can also be done for one stream within a session while keeping the rest of the session active. Termination is done by sending the Term message 290. This message can originate in gateway device 30 or application server 70. FIG. 17 illustrates the case where it originates from the application server. The Term message 290 contains the following information:

The source and destination addresses.
The source and destination communication ports.
The version of the protocol being used.
The session identifier.
The stream identifier parameter, which is included if one stream is being terminated while the session remains active.
Reason parameter, which specifies a reason for terminating the session.
Authentication and encryption data.

Upon receiving the Term message 290, the receiver constructs the Term_ack message 300 and sends it. The Term_ack message 300 contains the following information:

The source and destination addresses.
The source and destination communication ports.
The version of the protocol being used.
The session identifier.
Status parameter, which specifies the result of the operation. In some cases the termination operation may fail, which results in the sender repeating the process. However, in other cases the sender may ignore the operation's failure and simply terminate the session at its end.
Authentication and encryption data.

At any point in time after a session is established, application server 70 may send a command to gateway device 30 that can either demand a certain action from the gateway device or from medical device 10. If the command requests an action by medical device 10, it is relayed by gateway device 30 to medical device 10. The command may contain any action deemed necessary by the application server. For instance, application server 70 may need medical device 10 to perform a certain lifesaving action like defibrillation or other actions needed by the user. The command message 320 is illustrated in FIG. 18. The Command message 320 contains the following information:

The source and destination addresses.
The source and destination communication ports.
The version of the protocol being used.

The session identifier.

The stream identifier parameter, which is included if a stream is established and the Command message is related to the established stream.

Command parameter, which contains a description of the command sent from application server 70.

Authentication and encryption data.

The Command_ack message 330 is sent from gateway device 30 to acknowledge the reception of the command message 320. It contains the following information:

The source and destination addresses.

The source and destination communication ports.

The version of the protocol being used.

The session identifier.

The stream identifier parameter, which is included if it were included in the command message 320.

Status parameter which, specifies the success or failure of the operation and reason for failure.

Authentication and encryption data.

If the Command message 320 requested an action by medical device 10, gateway device 30 will relay the command to medical device 10 using the Comm message 340. The Comm message contains the following information:

The source and destination addresses.

The source and destination communication ports.

The version of the protocol being used.

The session identifier parameter, which includes the session identifier for the session set-up between medical device 10 and gateway device 30.

The message identifier.

Command parameter, which describes the command sent from application server 70.

Authentication and encryption data.

Medical device 10 acknowledges the reception of the Comm message 340 by sending the comm_ack message 350. The comm_ack message contains the following information:

The source and destination addresses.

The source and destination communication ports.

The version of the protocol being used.

The session identifier.

The message identifier.

Status parameter, which specifies success or failure and the reason for failure.

Authentication and encryption data.

Exemplary embodiments of the present invention allow application server 70 to detect the presence of a medical emergency that requires alerting a medical emergency service or physician, or a nominated person or all of the above. Detecting an emergency can take place if application server 70 is explicitly notified by gateway device 30 (possibly due to a notification by medical device 10) or by analysing the data sent from gateway device 30 and deciding that a medical emergency exists.

Gateway device 30 can indicate an emergency while sending medical information, relayed from medical device 10 or due to manual intervention by the user. On the other hand, application server 70 can detect an emergency by analysing the medical data coming from gateway device 30. Such analysis may be routinely made when a stream is set-up for certain types of devices (known from the application identifier) or due to a request by the user, or due to certain configuration on the user's account. For instance, a user that may need close attention (a recovering patient or a high risk one) may have an account configuration that requires continuous monitoring of all data sent from his or her medical device.

Depending on the settings in the user's account, an emergency situation may be handled differently. An application server may alert certain parties of the need for attention to the user's data. Alternatively, the application server may notify such parties as well as notifying an emergency service, e.g. ambulance service to get to the user. In the latter scenario, the user's location would be collected from the gateway device. The user's location can be obtained through the knowledge of the geographical location using a positioning system (e.g. satellite based systems like GPS or triangulation techniques in cellular networks), the Internet topology where the user is located, the access point to the Internet that the gateway device is connected to, or a combination of all of this information.

User records contain health information that is manually or automatically added by the user or gateway device 30, respectively. Examples of health information include the following:

Medical history: including the user's previous illness, surgeries, accidents or any other event in the past that affected the user's health.

Medications: including any prescription or non-prescription medication that the user is taking. This also includes allowing the user to renew prescriptions online.

Scans: including any scans received like X-rays, ultrasound information, CT-scans, MRI, and any other types of scans related to cardiology health.

Pathology: including any laboratory results done for the user.

Nutritional diary: including the user's nutritional diary, food consumption, the user's height and weight, and the amount of nutrients in the user's food, including calories. This record may also contain the ingredients of food consumed by the user.

Exercise diary: including the user's exercise diary, like running, swimming, walking or any other exercise activity. Each exercise session can contain several attributes related to the user's physical functions during exercise. A simple example of such attributes includes the user's heart rate. Such measurements can be taken regularly during exercise and sent to application server 70 from medical device 10, through gateway device 30.

Measurements: including any measurements related to the user's health that are added automatically by gateway device 30 or manually added by the user.

Family history: including any hereditary illnesses like heart disease, that affected the user's family members.

Doctor's comments: including any comments added by the user's physicians or health practitioners.

Toddler records: including information about toddlers in the user's family. This includes any information related to the toddler's health, height, weight, vaccinations, illness, and so on.

Subscribed Services: including the services that a user is subscribed to receive.

Biometric information: including any biometric information that can be used to identify the user. Examples include retinal scans, fingerprints, DNA information or any other information.

User's identification: including user identification information like scans of a driver's license, passport, or any other photographic or non-photographic identification.

Personal settings: including the user's personal settings and preferences. This may include display settings, language preferences, choice of whether the user wants to receive alerts other than those subscribed, and so on.

Medical library: including interesting articles that may be relevant to the user's medical records.

Each of the above headings within a user's record contains zero or more entries. Each entry has attributes that define read and write authorization. In other words, each entry can be read or modified based on the authorization level of the user. Hence, different entities viewing the user's record may be able to read or modify subsets of the record. As a result of this architecture, the record owner may associate different entities with different levels of authorization. This allows the record owner to allow different health practitioners to view different parts of his or her medical records.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A method for delivering telemedicine services, the method comprising:
    obtaining, by a medical device, diagnostic information;
    discovering, by the medical device, a gateway device, wherein the discovering includes an exchange of messages at a link layer, IP layer, or application layer, and the exchanged messages include
        the medical device transmitting a message to the gateway device announcing capabilities required to initiate communication, the announced capabilities including types of medical applications supported by the medical device, and
        the medical device receiving from the gateway device a message announcing capabilities of the gateway device;
    establishing, by the medical device, a connection with the gateway device;
    establishing, by the medical device, a session with the gateway device; and
    transferring, by the medical device, the diagnostic information to the gateway device.

2. The method of claim 1, further comprising:
    establishing, by gateway device, a connection with an application server;
    establishing, by the gateway device, a session with the application server; and
    transferring, by the gateway device, the diagnostic information to the application server.

3. The method of claim 2, further comprising:
    storing the diagnostic information in a database;
    analyzing the stored diagnostic information; and
    raising an alarm when the stored diagnostic information exceeds a predefined threshold, wherein the predefined threshold is customized on a per-user basis.

4. The method of claim 3, wherein the raising the alarm includes dialing an emergency service provider and providing a user's location and medical records.

5. The method of claim 3, wherein the diagnostic information is stored in an entry in the database that is uniquely indexed.

6. The method of claim 5, wherein the diagnostic information can be modified by a remote wired or wireless device.

7. The method of claim 3, wherein the diagnostic information is stored in the database as a user record, and user record includes information about health and wellness of a user including medical history, family history, toddler medical data, nutritional diary, health measurements, exercise diary, scans and laboratory results.

8. The method of claim 7, wherein read/write authorization levels are associated with each entry within the user's medical record.

9. The method of claim 1 wherein a plurality of sessions are established over the connection between the medical device and the gateway device.

10. The method of claim 1, wherein the gateway is a wireless device.

11. The method of claim 1, wherein a plurality of medical devices establish connections and sessions with the gateway device.

12. The method of claim 1, further comprising:
    receiving, by the medical device, a redirection message from the gateway device; and
    redirecting the diagnostic information to an element identified in the redirection message.

13. A method for delivering telemedicine services, the method comprising:
    obtaining, by a medical device, diagnostic information;
    discovering, by the medical device, a gateway device;
    establishing, by the medical device, a connection with the gateway device;
    establishing, by the medical device, a session with the gateway device;
    transferring, by the medical device, the diagnostic information to the gateway device;
        exchanging data between the medical and gateway devices; and
        performing flow control over the data exchange, wherein the flow control includes the medical device receiving a message from the gateway device instructing the medical device to slow down or temporarily stop information transfer to the gateway device.

14. A method for delivering telemedicine services, the method comprising:
    obtaining, by a medical device, diagnostic information;
    discovering, by the medical device, a gateway device;
    establishing, by the medical device, a connection with the gateway device;
    establishing, by the medical device, a session with the gateway device;
    transferring, by the medical device, the diagnostic information to the gateway device;
    establishing, by gateway device, a connection with an application server;
    establishing, by the gateway device, a session with the application server; and
    transferring, by the gateway device, the diagnostic information to the application server, wherein the gateway device establishes sessions in addition to the session with the application server, and diagnostic information is multicast by the gateway device over the session with the application server and the additional sessions.

* * * * *